US008754137B2

(12) United States Patent
Scholten et al.

(10) Patent No.: US 8,754,137 B2
(45) Date of Patent: Jun. 17, 2014

(54) METHANATION REACTION METHODS UTILIZING ENHANCED CATALYST FORMULATIONS AND METHODS OF PREPARING ENHANCED METHANATION CATALYSTS

(75) Inventors: Scott A. Scholten, Katy, TX (US); Joe D. Allison, Bartlesville, OK (US); Brian C. Dunn, Bartlesville, OK (US)

(73) Assignee: Phillips 66 Company, Houston, TX (US)

( * ) Notice: Subject to any disclaimer, the term of this patent is extended or adjusted under 35 U.S.C. 154(b) by 343 days.

(21) Appl. No.: 13/421,118

(22) Filed: Mar. 15, 2012

(65) Prior Publication Data

US 2012/0238647 A1 Sep. 20, 2012

Related U.S. Application Data

(60) Provisional application No. 61/454,219, filed on Mar. 18, 2011.

(51) Int. Cl.
 *C07C 27/00* (2006.01)
 *C07C 9/04* (2006.01)
 *C07C 1/12* (2006.01)

(52) U.S. Cl.
 CPC ... *C07C 9/04* (2013.01); *C07C 1/12* (2013.01); *C07C 2523/26* (2013.01); *C07C 2523/755* (2013.01)
 USPC .......................................... 518/715; 518/700

(58) Field of Classification Search
 CPC ............ C07C 27/00; C07C 1/12; C07C 9/04; C07C 2523/26; C07C 2523/755
 USPC .................................................. 518/700, 715
 See application file for complete search history.

(56) References Cited

U.S. PATENT DOCUMENTS

| 4,131,616 A | 12/1978 | Stiles |
| 4,185,967 A | 1/1980 | Komodromos et al. |
| 4,372,755 A | 2/1983 | Tolman et al. |
| 4,455,391 A | 6/1984 | Kitchener |
| 4,540,681 A | 9/1985 | Kustes et al. |
| 2010/0162626 A1 | 7/2010 | Clomburg, Jr. et al. |

OTHER PUBLICATIONS

"Sunlight Turns Carbon Dioxide to Methane," Mar. 5, 2009, 2 pages.
PCT Notification of Transmittal of the International Search Report and the Written Opinion of the International Search Authority, or the Declaration, International Application No. PCT/US2012/029257, International Filing Date: Mar. 15, 2012, 9 pages.

*Primary Examiner* — Jafar Parsa
(74) *Attorney, Agent, or Firm* — Phillips 66 Company

(57) ABSTRACT

Enhanced mixed metal catalysts are provided which allow high conversions of carbon dioxide to methane, in some cases up to about 100% conversion. Methods of preparing enhanced mixed metal catalysts comprise a series of steps involving combining nickel and chromium salts with a nucleation promoter in a base environment to form a gel, allowing the gel to digest to form a solid and a mother liquor, isolating the solid, washing the solid, drying the solid, and thermally treating the solid to form a nickel-chromium catalyst. Methanation processes using the catalysts are also provided. The enhanced mixed metal catalysts provide more efficient conversion and lower operating temperatures for carbon dioxide methanation when compared to conventional methanation catalysts. Additionally, these enhanced catalyst formulations allow realization of higher value product from captured carbon dioxide.

27 Claims, No Drawings

METHANATION REACTION METHODS UTILIZING ENHANCED CATALYST FORMULATIONS AND METHODS OF PREPARING ENHANCED METHANATION CATALYSTS

CROSS-REFERENCE TO RELATED APPLICATIONS

This application is a non-provisional application which claims the benefit of and priority to U.S. Provisional Application Ser. No. 61/454,219 filed Mar. 18, 2011, entitled "Methanation Reaction Methods Utilizing Enhanced Catalyst Formulations and Methods of Preparing Enhanced Methanation Catalysts," which is hereby incorporated by reference in its entirety.

BACKGROUND OF THE INVENTION

The accumulation of greenhouse gases such as carbon dioxide in the atmosphere is known to contribute to global warming due to the greenhouse effect. Reducing greenhouse gases in the atmosphere remains a continuing global concern. Unfortunately, despite efforts at reducing carbon dioxide emissions, carbon dioxide concentrations in the atmosphere continue to rise annually primarily due to fossil fuel combustion. The United States Environmental Protection Agency (EPA) estimates that the global atmospheric concentrations of carbon dioxide were 35% higher in 2005 than they were before the Industrial Revolution.

Reducing carbon dioxide emissions has traditionally focused on either reducing fossil fuel combustion or sequestration of carbon dioxide. Sequestration of carbon dioxide is the process of removing carbon from the atmosphere and depositing it in a reservoir. It is a geoengineering technique for long-term storage of carbon dioxide or other forms of carbon to either mitigate or defer global warming. By capturing carbon dioxide as a by-product in processes related to petroleum refining or from flue gases from power generation, the carbon dioxide may be sequestered in this way for long term storage in permanent artificial reservoirs such as subsurface saline aquifers, reservoirs, ocean water, aging oil fields, or other carbon sinks.

Another way of taking advantage of carbon dioxide production is by converting the carbon dioxide to a higher value product. Methanation reactions are one example of a reaction process for converting carbon dioxide to a more desirable product, in this case, methane. Although carbon dioxide may be reacted to produce higher value products, such processes have traditionally been uneconomical due to the low reaction yields inherent in such processes and inefficiencies of current reaction methodologies. Conventional carbon dioxide methanation processes generally require high temperatures to achieve reasonable yields and consequently result in high energy usage. The high reaction temperatures also result in high capital equipment investment for conventional methanation processes. Thus, conventional carbon dioxide methanation processes are plagued with low efficiencies and high costs.

The proposed U.S. Federal cap and trade legislation may further support the economics of carbon dioxide capture and sequestration or alternatively processes that convert carbon dioxide to useful products. Where emission credits are offered for the capture of carbon dioxide, these emission credits enhance the economics of converting carbon dioxide to a more valuable product.

Methanation is typically accomplished through the conversion of carbon monoxide over a conventional nickel catalyst to methane as described by the following chemical reaction:

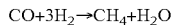

The chemical reaction of carbon dioxide to methane is depicted as follows:

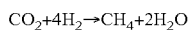

Achieving desirable reaction in methanation reactions typically requires temperatures exceeding approximately 230° C. using conventional catalysts. This high temperature means that reaction vessels for these reactions must be fabricated out of metallurgies able to withstand the high temperatures or alternatively, one must stage the reaction over multiple reactors in series. In other words, the high temperatures required to achieve economically satisfactory completion of the methanation reactions essentially require either higher capital costs or higher operating costs. The high capital costs are due to having to use reactor metallurgies capable of withstanding the higher temperatures involved or having to stage multiple reactors in series. Where such higher temperatures are avoided by additional cooling equipment, higher operating costs are necessarily incurred.

Another disadvantage of conventional catalysts is the higher coke formation inherent in the use of these conventional catalysts. Catalyst deactivation via coke deposition occurs with any carbon-containing source when oxygen is not present in the stream. The rate of coke deposition is strongly dependent on reaction temperature with higher deposition rates at higher temperatures. Operation at lower temperatures favors slower deposition rates, hence, less deactivation.

Thus, conventional catalysts are deficient in that they lack the ability to satisfactorily complete methanation reactions at sufficiently low temperatures. Consequently, conventional catalysts currently available for methanation reactions fail to realize satisfactory economic results.

SUMMARY

The present invention relates to improved methanation reaction methods utilizing enhanced catalyst formulations and methods of preparing enhanced methanation catalysts.

One example of a methanation reaction process comprises the steps of: preparing a nickel-chromium catalyst, wherein the step of preparing comprises the steps of: (a) combining a nickel(II) salt and a chromium(III) salt with a nucleation promoter and ammonium hydroxide to form a gel, the gel comprising a solid and a liquid; (b) allowing the gel to digest to form a mother liquor and an isolatable solid; (c) isolating the solid from the mother liquor; (d) washing the solid; (e) drying the solid; (f) thermally treating the solid to form the nickel-chromium catalyst; wherein steps (a)-(f) result in a nickel/chromium ratio of about 98:2 to about 50:50 in the nickel-chromium catalyst; providing a single reactor vessel; continuously introducing carbon dioxide and hydrogen gas into the single reactor vessel over a fixed bed, the fixed bed comprising the nickel-chromium catalyst; allowing the carbon dioxide and hydrogen gas to react in the single reactor vessel at a conversion rate in the presence of the nickel-chromium catalyst at a reaction temperature; maintaining the reaction temperature in the single reactor vessel at about 205° C. to about 220° C. by controlling a flow rate of one of the carbon dioxide and the hydrogen gas fed to the single reactor vessel; and wherein the conversion rate to methane is about 25 percent to about 100 percent.

One example of a methanation reaction method comprises the steps of: (a) providing a nickel-chromium catalyst, the nickel-chromium catalyst having a nickel/chromium ratio of about 98:2 to about 50:50; (b) providing a single reactor vessel; (c) introducing carbon dioxide and hydrogen gas into the single reactor vessel; (d) allowing the carbon dioxide and hydrogen gas to react at a conversion rate in the presence of the nickel-chromium catalyst in the single reactor vessel at a reaction temperature; (e) maintaining the reaction temperature in the single reactor vessel at about 205° C. to about 220° C.; and (f) wherein the conversion rate to methane is about 100 percent.

The features and advantages of the present invention will be apparent to those skilled in the art. While numerous changes may be made by those skilled in the art, such changes are within the spirit of the invention.

DETAILED DESCRIPTION

The present invention relates to improved methanation reaction methods utilizing enhanced catalyst formulations and methods of preparing enhanced methanation catalysts.

Methanation of carbon dioxide is typically accomplished over a nickel catalyst to methane as described in the following chemical reaction:

$$CO_2 + 4H_2 \rightarrow CH_4 + 2H_2O$$

One conventional catalyst used to achieve this methanation reaction is the Haldor-Topsoe methanation catalyst PK-7R. This conventional catalyst is advertised as a low-temperature carbon monoxide methanation catalyst with operation temperatures down to 190° C. while maintaining 100% conversion. When the PK-7R catalyst is employed in carbon dioxide methanation (as opposed to carbon monoxide methanation), testing performance of the PK-7R catalyst reveals that 100% conversion is only achieved at temperatures exceeding approximately 230° C. Testing of other nickel oxide methanation catalysts achieved similar results. Accordingly, conventional methanation catalysts only achieve 100% carbon dioxide conversions at unacceptably high temperatures.

Conventional methanation catalysts have been optimized to convert feeds containing primarily carbon monoxide. To date, no conventional catalysts have been optimized for methanation feeds primarily composed of carbon dioxide to the inventor's knowledge.

The methods disclosed herein provide an enhanced mixed metal catalyst which may lead to energy savings by lowering the operating temperature of carbon dioxide methanation. In particular, the addition of chromium may promote the reverse water gas shift reaction which is described by the following chemical reaction:

$$CO_2 + H_2 \rightarrow CO + H_2O$$

In certain embodiments, the enhanced mixed metal methanation catalyst disclosed herein demonstrates methanation of carbon dioxide with 100% conversion at approximately 210° C., which represents a 20° C. improvement over other conventional commercial catalysts tested. At lower reaction conversions, the enhanced mixed metal methanation catalyst provides even lower reaction temperatures, resulting in further economic savings. These lower reaction temperatures translate into reduced operating costs and/or lower equipment capital costs depending on reactor design.

Reference will now be made in detail to embodiments of the invention. Each example is provided by way of explanation of the invention, not as a limitation of the invention. It will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention cover such modifications and variations that come within the scope of the invention.

Methods of Preparing Enhanced Mixed Metal Methanation Catalysts

Methods of preparing mixed metal methanation catalysts of the present invention comprise a series of steps involving combining nickel and chromium salts with a nucleation promoter in a base environment to form a gel, allowing the gel to digest to form a mother liquor and an isolatable solid, isolating the solid from the mother liquor, washing the solid, drying the solid, and thermally treating the solid to form a nickel-chromium catalyst.

More particularly, one example of preparing an enhanced mixed metal methanation catalyst of the present invention begins with combining a nickel(II) salt and a chromium(III) salt with a nucleation promoter in an aqueous solution. In some embodiments, the nickel(II) salt comprises nickel(II) nitrate hexahydrate, and the chromium(III) salt comprises chromium(III) nitrate hexahydrate, although any suitable anion may be used to form the nickel(II) and chromium(III) salts as desired. Combining the nickel(II) and chromium(III) salts with the nucleation promoter in an aqueous solution allows for intimate mixing of the two active metals and a high surface area from the nucleation promoter. In certain embodiments, the aqueous solution thus prepared contains about 1 wt % to about 40 wt % nucleation promoter. In certain embodiments, the concentration of nucleation promoter is about 40 wt %.

The nucleation promoter may comprise any substance suitable to promote nucleation of the precipitating catalyst precursor. Substances suitable for promoting nucleation include any substance that has a high surface area (at least about 1 $m^2/g$), is inert (e.g. is not chemically reactive with any of the other components), and is thermally stable through the range of temperatures to which the substance will be exposed. Examples of suitable nucleation promoters include colloidal silica, alumina, amorphous silica-alumina, natural and synthetic zeolites, carbon, zirconia, silicon carbide, and titania.

After combining the nickel(II) and chromium(III) salts with the colloidal silica in an aqueous solution, a base (in solution or otherwise) may be added to the aqueous solution to form a gel. In certain embodiments, the base comprises ammonium hydroxide, although other bases may be used.

In other embodiments, the aqueous solution and base may be added simultaneously to a quantity of water. In certain embodiments, the flow rate of the base (in solution or otherwise) may be modulated at a rate sufficient to maintain a pH in the resulting solution of about 7.5 to about 10. A target pH of about 9 is preferred in some embodiments. An additional water stream may be added during this step if desired. It is also recognized that the base could be added simultaneously with the step of combining the nickel(II) and chromium(III) salts with the colloidal silica.

After forming the gel, the gel may be allowed to digest. Digesting of the gel allows the formed small particles to "ripen" achieving the size necessary to isolate the solid from the mother liquor through simple, inexpensive separation methods such as filtration, centriguation, decantation, or other suitable separation methods. In certain embodiments, the gel is allowed to digest at about 50° C. to about 80° C. for a period of time of from about half an hour to about 12 hours. In some embodiments, it is preferred to allow the gel to digest at a temperature of about 60° C. for about an hour. Any heat source may be used to maintain temperature of the gel during the digesting step.

The gel, which comprises a liquid and a solid, is treated to isolate the solid from the liquid. In certain embodiments, the isolation is accomplished by vacuum filtration. The solid thus collected may then be washed with a solvent, such as water, to remove any excess ammonium hydroxide, non-hydroxide metals, and any other contaminants The filtration and washing steps may be repeated several times to remove undesired impurities. In certain embodiments, the filtration and washing steps are repeated a minimum of three times.

The solid thus isolated may then be dried to remove excess moisture. In certain embodiments, the drying step may be accomplished by placing the solid an oven maintained at the desired temperature or by flowing heated air over the solid for about 12 hours at about 120° C. In some embodiments, it may be preferred to dry the solids at conditions sufficient to dry the solid to less than about $1\%_{wt}$ water. In certain embodiments, it may be preferred to dry the solids to less than about 0.01 wt % water.

Upon sufficient drying of the solid, the solid may be thermally treated to form a nickel-chromium catalyst. In certain embodiments, the thermal treatment of the solid comprises the step of calcining the solid by placing the solid in a furnace, maintaining an atmosphere of flowing air, and raising the temperature to between about 300° C. to about 450° C. at a rate of about 2° C./min to about 5° C./min, and maintaining the temperature for a period of time sufficient to decompose any nitrate or hydroxide salts. In some embodiments, the period of time is about 4 hours to about 6 hours. Calcining converts the metal nitrates and hydroxides into metal oxides. This step prepares the catalyst into a state ready for activation inside the reactor.

It is recognized that it is possible to combine the drying and thermal treating steps if desired. The nickel-chromium catalyst thus formed may be cooled to ambient temperature upon completion of the thermal treatment.

The quantities of reagents may be chosen to result in a nickel/chromium ration of about 98:2 to about 50:50. In certain embodiments, the component quantities are chosen to result in a nickel/chromium ration of about 80:20.

The nickel/chromium oxide catalyst formed by the above steps is reduced to an active reduced metal catalyst prior to use as a reaction catalyst. This reduction of the nickel/chromium oxide catalyst to an active reduced metal catalyst may be achieved by reducing the nickel/chromium oxide catalyst in a reducing atmosphere such as hydrogen. This reduction allows formation of the zero-valent state necessary for catalytic operation.

Additionally, the enhanced catalyst may be reduced in size to particulates to increase the surface area available for use. In certain embodiments, the solid is subjected to grinding and sieving operations that reduce the solid to particulates in the range of about 20 mesh to about 40 mesh. In some embodiments, the particulates have an average particulate size between about 25 to 35 mesh.

Methanation Reactions and Methods of Use

The enhanced mixed metal catalysts prepared according to the methods disclosed herein allow for a more efficient methanation of carbon dioxide, allowing high conversion of carbon dioxide at temperatures significantly lower than those of conventional catalysts.

One example of a method for methanation of carbon dioxide comprises the steps of preparing an enhanced mixed metal nickel-chromium catalyst according to the methods disclosed herein, providing the catalyst in a single reactor vessel, supplying carbon dioxide and hydrogen feed to the reactor, allowing the carbon dioxide and hydrogen gas to react in the presence of the catalyst, and maintaining a reaction temperature of about 205° C. to about 220° C. As demonstrated by the examples below, conversions around 100% are achievable when using the enhanced mixed metal catalysts of the present invention for methanation of carbon dioxide.

In certain embodiments, the ratio of hydrogen to carbon dioxide is 4:1. Higher $H_2:CO_2$ ratios will have no impact on the catalyst but will result in unnecessary capital expense from the required recycling of the excess hydrogen. Lower ratios promote formation of byproduct carbon monoxide.

A fixed bed of catalyst may be maintained in the reactor such as for example by a catalyst support plate in proximity of the reactor outlet. Other physical configurations are possible.

As described above, useful ratios of nickel-chromium in the enhanced mixed-metal catalyst include ratios of about 98:2 to about 50:50 nickel/chromium.

It is explicitly recognized that any of the elements and features of each of the devices described herein are capable of use with any of the other devices described herein with no limitation. Furthermore, it is explicitly recognized that the steps of the methods herein may be performed in any order except unless explicitly stated otherwise or inherently required otherwise by the particular method.

Examples

Example 1

Enhanced Mixed Metal Catalyst Preparation

A nickel/chromium precipitated catalyst was prepared for carbon dioxide methanation according to the following procedure to produce a final oxide mass of 30 grams.

The following reagents were used to prepare the enhanced mixed metal catalyst:

129.1255 g nickel (II) nitrate hexahydrate
28.5979 g chromium(III) nitrate hexahydrate
5.643 g Ludox® AS-40 40 wt % silica
102.654 g ammonium hydroxide solution, 28 wt %, Step 1. Add ammonium hydroxide solution to about 600 mL of deionized water in a beaker.

Step 2. Dissolve solid nickel(II) nitrate hexahydrate and chromium(III) nitrate hexahydrate in about 400 g of deionized water.

Step 3. Add the Ludox® AS-40 silica to the nickel (II) nitrate/chromium (III) nitrate solution prepared above in step 2.

Step 4. Add 600 g of deionized water to a 2 liter beaker. Stir with overhead stirrer at 300 rpm and place pH probe in water.

Step 5. Using tubing pumps, add both solutions to the water at about 5.0 mL/min. Maintain pH at about 9 by adjusting the rate of ammonium hydroxide solution addition.

Step 6. Digest the solid at about 60° C. for about 60 minutes.

Step 7. Collect solid by vacuum filtration. Wash solid by transferring the solid to a 2 liter beaker, adding about 1 liter of deionized water and stirring with overhead stirrer until all large solid pieces are broken apart.

Step 8. Repeat filtration and washing until a total of three washings have been competed.

Step 9. Dry at 120° C. for about 8 to about 12 hours.

Step 10. Calcine by heating in a furnace with flowing air at about 0.3 L/min to about 350° C. at about 2.0° C./min. Hold at a temperature of about 350° C. for 240 minutes, Step 11. Cool in furnace with flowing air.

Step 12. Collect and weigh.

Step 13. Size the solid to particulates from about 20 mesh to about 40 mesh through successive grinding and sieving operations.

This procedure produced an oxide mass of about 30 grams with a nickel/chromium ration of about 80:20.

Example 2

Carbon Dioxide Conversion to Methane

Methanation experiments over 3 g of Ni/Cr catalyst synthesized according to Example 1 above indicate 100% carbon dioxide conversion is maintained at catalyst bed temperatures down to 207° C. and occurs in a stoichiometric ratio with little likely coke formation.

In order to access the potential advantages of Ni/Cr on $CO_2$ methanation, three $NiO_2$ catalysts were studied in a 316 SS ¾" O.D. fixed-bed catalyst reactor inside of a ventilated enclosure.

The first catalyst was synthesized according to Example 1 above but omitting the chromium (III) nitrate hexahydrate. The second was a Katalco pelletized $NiO_2$ crushed and sized to 20-40 mesh. The third was the Haldor Topsoe low temperature $NiO_2$ methanation catalyst PK-7R crushed and sized to 20-40 mesh. Each 3 g sample was tested for minimum temperature needed to maintain 100% carbon dioxide conversion at conditions of 450 psig, 25 sccm $CO_2$ and 100 sccm $H_2$. The resulting minimum temperatures required for 100% carbon dioxide conversion were as follows:

COP $NiO_2$>250° C.

Katalco $NiO_2$>227° C.

PK-7R $NiO_2$>229° C.

Accordingly, as the enhanced mixed metal catalyst achieves 100% carbon dioxide conversion at only 207° C. in this experiment (as opposed to >250° C., >227° C., and >229° C. for the conventional catalysts), this experiment demonstrates the efficacy of enhanced mixed metal catalysts as compared to conventional catalysts for the methanation of carbon dioxide. As the conventional methanation catalysts are designed for conversion of carbon monoxide to methane, they are not optimized for conversion of carbon dioxide to methane as demonstrated by this experiment.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations and equivalents are considered within the scope and spirit of the present invention. Also, the terms in the claims have their plain, ordinary meaning unless otherwise explicitly and clearly defined by the patentee.

What is claimed is:

1. A methanation reaction process comprising the steps of:
preparing a nickel-chromium catalyst, wherein the step of preparing comprises the steps of:
(a) combining a nickel(II) salt and a chromium(III) salt with a nucleation promoter and ammonium hydroxide to form a gel, the gel comprising a solid and a liquid;
(b) allowing the gel to digest to form a mother liquor and an isolatable solid;
(c) isolating the solid from the mother liquor;
(d) washing the solid;
(e) drying the solid;
(f) thermally treating the solid to form the nickel-chromium catalyst;
wherein steps (a)-(f) result in a nickel/chromium ratio of about 98:2 to about 50:50 in the nickel-chromium catalyst;
providing a single reactor vessel;
continuously introducing carbon dioxide and hydrogen gas into the single reactor vessel over a fixed bed, the fixed bed comprising the nickel-chromium catalyst;
allowing the carbon dioxide and hydrogen gas to react in the single reactor vessel at a conversion rate in the presence of the nickel-chromium catalyst at a reaction temperature;
maintaining the reaction temperature in the single reactor vessel at about 205° C. to about 220° C. by controlling a flow rate of one of the carbon dioxide and the hydrogen gas fed to the single reactor vessel; and
wherein the conversion rate to methane is about 25 percent to about 100 percent.

2. The process of claim 1 wherein the nickel(II) salt comprises nickel(II) nitrate hexahydrate and wherein the chromium(III) salt comprises chromium(III) nitrate hexahydrate.

3. The process of claim 2 wherein the conversion rate is about 90 to about 100 percent.

4. The process of claim 3 wherein the conversion rate is about 95 to about 100 percent.

5. The process of claim 4 wherein the conversion rate is about 97 to about 100 percent.

6. The process of claim 1 wherein the nucleation promoter is an inert substance having a surface area greater than about 1 $m^2$/g wherein the nucleation promoter is thermally stable up to about 220° C.

7. The process of claim 6 wherein the nucleation promoter is colloidal silica.

8. The process of claim 1 wherein the combining of step (a) further comprises the steps of:
(i) combining the nickel(II) salt, the chromium(III) salt, and the colloidal silica in an aqueous solution;
(ii) adding the ammonium hydroxide and the aqueous solution to a quantity of water to form a resulting solution and modulating the addition of the ammonium hydroxide at a flow rate sufficient to maintain a target pH of the resulting solution of about 7.5 to about 10; and
wherein step (ii) occurs after step (i).

9. The process of claim 8 wherein the target pH is about 9.

10. The process of claim 2 wherein step (c) further comprises the step of allowing the gel to digest at about 50° C. to about 80° C. for about 0.5 hours to about 12 hours.

11. The process of claim 10 wherein step (c) further comprises the step of allowing the gel to digest at about 60° C. for about 1 hour.

12. The process of claim 11 further comprising the steps of washing the solid with water and filtering the solid from the water.

13. The process of claim 12 wherein step (d) comprises the step of drying the solid at conditions sufficient to dry the solid to less than about 1% water.

14. The process of claim 13 wherein step (d) comprises the step of drying the solid for about 12 hours at about 120° C.

15. The process of claim 13 wherein the nickel(II) salt comprises nickel(II) nitrate hexahydrate and wherein the chromium(III) salt comprises chromium(III) nitrate hexahydrate and wherein step (f) comprises the step of thermally treating the solid to form the nickel-chromium catalyst by heating in a furnace with continuously flowing air and raising the temperature to between about 300° C. to about 450° C. at a rate of about 2° C./min to about 5° C./min and maintaining the temperature for a sufficient period of time to decompose any hydroxide and nitrate salts.

16. The process of claim 15 wherein the period of time to decompose the hydroxide and nitrate salts is about 4 to about 6 hours.

17. The process of claim 15 further comprising the step of cooling to about ambient temperature the nickel-chromium catalyst with flowing air.

18. The process of claim 15 wherein the nickel/chromium ratio in nickel-chromium catalyst is about 80:20.

19. The process of claim 15 wherein the conversion rate to methane is about 100 percent.

20. A methanation reaction method comprising the steps of:
   (a) providing a nickel-chromium catalyst, the nickel-chromium catalyst having a nickel/chromium ratio of about 98:2 to about 50:50;
   (b) providing a single reactor vessel;
   (c) introducing carbon dioxide and hydrogen gas into the single reactor vessel;
   (d) allowing the carbon dioxide and hydrogen gas to react at a conversion rate in the presence of the nickel-chromium catalyst in the single reactor vessel at a reaction temperature;
   (e) maintaining the reaction temperature in the single reactor vessel at about 205° C. to about 220° C.; and
   (f) wherein the conversion rate to methane is about 100 percent.

21. The method of claim 20 further comprising a step of reduction of the nickel/chromium catalyst, wherein the step of reduction comprises reducing a nickel/chromium oxide catalyst in a reducing atmosphere to reduce the nickel/chromium oxide catalyst to an active reduced metal catalyst prior to step (c).

22. The method of claim 21 wherein the nickel/chromium ratio in step (a) is about 80:20.

23. The method of claim 22 wherein the step (c) further comprises continuously introducing carbon dioxide and hydrogen gas into the single reactor vessel and wherein the nickel-chromium catalyst is supported in a fixed-bed arrangement.

24. The method of claim 23 wherein the step of maintaining the reaction temperature in step (e) is achieved by controlling a flow rate of one of the carbon dioxide and the hydrogen gas fed to the single reactor vessel.

25. The method of claim 24 further comprising preparing the nickel-chromium catalyst wherein the step of preparing comprises the steps of:
   (a) combining a nickel(II) nitrate hexahydrate and a chromium(III) nitrate hexahydrate, and colloidal silica in an aqueous solution;
   (b) controlling a first flow rate of ammonium hydroxide and a second flow rate of the aqueous solution to a quantity of water to form a gel, the gel comprising a solid and a liquid;
   (c) limiting the first flow rate of ammonium hydroxide to maintain the gel at a pH of about 8 to about 10;
   (d) allowing the gel to digest to form a mother liquor and an isolatable solid;
   (e) isolating the solid from the mother liquor;
   (f) washing the solid with water;
   (g) filtering the solid from the water;
   (h) drying the solid; and
   (i) thermally treating the solid to form the nickel-chromium catalyst.

26. The method of claim 25:
   wherein step (d') further comprises the step of allowing the gel to digest at about 60° C. to about 70° C. for about 0.5 hours to about 2 hours;
   wherein step (h') further comprises drying the solid comprises at conditions sufficient to dry the solid to less than about 1% water;
   wherein step (i') further comprises the step of calcining the solid wherein the step of calcining comprises the step of continuously flowing heated air over the catalyst and raising the temperature to between about 300° C. to about 450° C. at a rate of about 2° C./min to about 5° C./min and maintaining the temperature for a sufficient period of time to decompose any hydroxide and nitrate salts; and
   further comprising the steps of grinding and sieving the nickel-chromium catalyst to form nickel-chromium catalyst in the form of about 20 to about 40 mesh particulates.

27. The method of claim 26 wherein the nickel-chromium catalyst has an average particulate size of about 20 to about 40 mesh particulates.

* * * * *